United States Patent
Li

(10) Patent No.: US 11,202,613 B2
(45) Date of Patent: Dec. 21, 2021

(54) BOLUS TRACKING

(71) Applicant: Neusoft Medical Systems Co., Ltd., Liaoning (CN)

(72) Inventor: Wei Li, Shenyang (CN)

(73) Assignee: Neusoft Medical Systems Co., Ltd., Liaoning (CN)

(*) Notice: Subject to any disclaimer, the term of this patent is extended or adjusted under 35 U.S.C. 154(b) by 474 days.

(21) Appl. No.: 16/168,190

(22) Filed: Oct. 23, 2018

(65) Prior Publication Data

US 2019/0117182 A1 Apr. 25, 2019

(30) Foreign Application Priority Data

Oct. 25, 2017 (CN) .......................... 201711009555.2

(51) Int. Cl.
A61B 5/00 (2006.01)
A61B 6/00 (2006.01)
A61M 5/00 (2006.01)
A61B 6/03 (2006.01)

(52) U.S. Cl.
CPC .............. A61B 6/542 (2013.01); A61B 6/032 (2013.01); A61B 6/481 (2013.01); A61B 6/54 (2013.01); A61M 5/007 (2013.01); A61B 6/469 (2013.01)

(58) Field of Classification Search
CPC ........... A61B 6/542; A61B 6/481; A61B 6/54; A61B 6/032; A61B 6/469; A61M 5/007
See application file for complete search history.

(56) References Cited

U.S. PATENT DOCUMENTS 7,145,982 B2 * 12/2006 Ikeda ..................... A61B 6/032
378/16
7,221,729 B2 * 5/2007 Wakai .................... A61B 6/032
378/108

(Continued)

FOREIGN PATENT DOCUMENTS

| CN | 1488317 A | 4/2004 |
|----|-----------|--------|
| CN | 1846623 A | 10/2006 |
| CN | 101502422 A | 8/2009 |

(Continued)

OTHER PUBLICATIONS

Bolus tracking; Wikipedia; https://en.wikipedia.org/wiki/Bolus_tracking; 4 pages.

(Continued)

Primary Examiner — Joel Lamprecht
(74) Attorney, Agent, or Firm — Fish & Richardson P.C.

(57) ABSTRACT

In a CT scanning method of bolus tracking, multiple CT scans are performed on a region of interest (ROI) of a subject while a contrast agent is injected into the subject. In a tracking process of the contrast agent, first and second CT values of the ROI of the subject for first and second CT scans are respectively obtained. If the second CT value is no less than a target threshold, the tracking process is finished. If the second CT value is less than the target threshold, an interval for increasing the second CT value to the target threshold is determined according to the first and second CT values and a first CycleTime representing a duration between starts of the first and second scans. Then a second CycleTime is set based on the interval, and a third scan is performed according to the second CycleTime.

18 Claims, 2 Drawing Sheets

S101
Obtain a first CT value $HU_1$ of the ROI for a first CT scan

S102
Perform an i-th tracking process, where i is an integer from 2 to N and N is an integer greater than or equal to 2

(56) References Cited

U.S. PATENT DOCUMENTS 8,126,109 B2 * 2/2012 Tsukagoshi ............ A61B 6/542
378/8
10,159,454 B2 * 12/2018 Grant ..................... A61B 6/486

FOREIGN PATENT DOCUMENTS

| CN | 102988071 A | 3/2013 |
| CN | 104138268 A | 11/2014 |
| CN | 104688259 A | 6/2015 |
| JP | 2007275360 A | 10/2007 |

OTHER PUBLICATIONS

State Intellectual Property Office of the People's Republic of China, Office Action and Search Report Issued in Application No. 2017110095552, dated Apr. 1, 2020, 16 pages, (Submitted with Machine Translation).

* cited by examiner

BOLUS TRACKING

CROSS REFERENCE TO RELATED APPLICATIONS

This application claims priority to Chinese Patent Application No. 201711009555.2 and filed on Oct. 25, 2017, the entire content of which is incorporated herein by reference.

BACKGROUND

Bolus tracking is a technique used in computed tomography (CT) imaging, such as angiography. In the bolus tracking technique, a tracking process is performed while a contrast agent is being injected into a subject along vein of the subject. The tracking process refers to multiple CT scans that are performed while the contrast agent is being injected into the subject. When a concentration of the contrast agent in the subject reaches a target concentration, a routine CT scan is performed to obtain a CT image for diagnosis. In this case, blood vessels in the CT image are relatively clearer, such that the medical personnel can better acknowledge the blood supply condition of the blood vessels and peripheral tissue.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods and devices for bolus tracking in computed tomography (CT) imaging.

One aspect of the present disclosure features a CT scanning method of bolus tracking, in which multiple CT scans are performed on an interest of region (ROI) of a subject while a contrast agent is injected into the subject, to perform a tracking process of the contrast agent. The method includes: obtaining a first CT value of the ROI of the subject for a (i−1)-th CT scan, where i is an integer greater than or equal to 2; obtaining a second CT value of the ROI of the subject for an i-th CT scan, where a first CycleTime $T_{i-1}$ represents a duration between a start of the i-th CT scan and a start of the (i−1)-th CT scan, and $T_1$ is preset; determining whether the second CT value is no less than a target threshold; and in response to determining that the second CT value is less than the target threshold, determining an interval according to the second CT value, the first CT value and the first CycleTime $T_{i-1}$, where the interval is configured for increasing the second CT value to the target threshold; setting a second CycleTime $T_i$ according to the interval and the first CycleTime $T_{i-1}$, where the second CycleTime $T_i$ represents a duration between the start of the i-th CT scan and a start of a (i+1)-th CT scan; and performing the (i+1)-th CT scan according to the second CycleTime $T_i$.

In some implementations, setting the second CycleTime $T_i$ according to the interval and the first CycleTime $T_{i-1}$ includes: in response to determining that the interval is greater than $2*T_{i-1}$, setting the second CycleTime $T_i$ to be a value greater than the first CycleTime $T_{i-1}$. In some cases, the value greater than the first CycleTime $T_{i-1}$ can be a sum of the first CycleTime $T_{i-1}$ and a preset variable, and the preset variable can decrease gradually as a number of CT scans performed on the ROI of the subject increases. In some cases, the first CycleTime $T_{i-1}$ is increased according to a preset ratio to obtain the value greater than the first CycleTime $T_{i-1}$, and the preset ratio decreases gradually as a number of CT scans performed on the ROI of the subject increases.

In some implementations, setting the second CycleTime $T_i$ according to the interval and the first CycleTime $T_{i-1}$ includes: in response to determining that the interval is greater than $T_{i-1}$ and less than $2*T_{i-1}$, setting the second CycleTime $T_i$ to be the first CycleTime $T_{i-1}$.

In some implementations, setting the second CycleTime $T_i$ according to the interval and the first CycleTime $T_{i-1}$ includes: in response to determining that the interval is less than $T_{i-1}$, setting the second CycleTime $T_i$ to be the interval.

Determining the interval according to the second CT value, the first CT value and the first CycleTime $T_{i-1}$ can include: obtaining a CT value increasing speed according the second CT value, the first CT value and the first CycleTime $T_{i-1}$; and determining the interval according to the CT value increasing speed, the second CT value, and the target threshold.

The method can further include: before injecting the contrast agent into the subject, performing a pilot scan on the subject to obtain a pilot image and determining the ROI according to the pilot image. The method can also include: determining that the tracking process in finished when a CT value of the ROI of the subject obtained for a CT scan is no less than the target threshold, and in response, stopping injecting the contrast agent and performing a routine CT scan to obtain a CT image of the ROI for diagnosis. For each of the CT scans, a CT value of the ROI can be a mean value of respective CT values of pixels in the ROI.

Another aspect of the present disclosure features a device for bolus tracking, including: at least one processor; and at least one non-transitory machine-readable storage medium coupled to the at least one processor having machine-executable instructions stored thereon that, when executed by the at least one processor, cause the at least one processor to perform operations for bolus tracking, in which multiple CT scans are performed on an interest of region (ROI) of a subject while a contrast agent is injected into the subject, to perform a tracking process of the contrast agent. The operations include: obtaining a first CT value of a ROI of a subject for a (i−1)-th CT scan, where i is an integer greater than or equal to 2; obtaining a second CT value of the ROI of the subject for an i-th CT scan, where a first CycleTime $T_{i-1}$ represents a duration between a start of the i-th CT scan and a start of the (i−1)-th CT scan, and T1 is preset; determining whether the second CT value is no less than a target threshold; in response to determining that the second CT value is greater than or equal to a target threshold, finish the tracking process; and in response to determining that the second CT value is less than the target threshold, determining an interval according to the second CT value, the first CT value and the first CycleTime $T_{i-1}$, where the interval is configured for increasing the second CT value to the target threshold; setting a second CycleTime $T_i$ according to the interval and the first CycleTime $T_{i-1}$, where the second CycleTime $T_i$ represents a duration between the start of the i-th CT scan and a start of a (i+1)-th CT scan; and performing the (i+1)-th CT scan according to the second CycleTime $T_i$.

In some implementations, setting the second CycleTime $T_i$ according to the interval and the first CycleTime $T_{i-1}$ includes: in response to determining that the interval is greater than $2*T_{i-1}$, setting the second CycleTime $T_i$ to be a value greater than the first CycleTime $T_{i-1}$. In some cases, the value greater than the first CycleTime $T_{i-1}$ is a sum of the first CycleTime $T_{i-1}$ and a preset variable, and the preset variable decreases gradually as a number of CT scans performed on the ROI of the subject increases. In some cases, the first CycleTime $T_{i-1}$ is increased according to a preset ratio to obtain the value greater than the first CycleTime $T_{i-1}$, and the preset ratio decreases gradually as a number of CT scans performed on the ROI of the subject increases.

In some implementations, setting the second CycleTime $T_i$ according to the interval and the first CycleTime $T_{i-1}$ includes: in response to determining that the interval is greater than $T_{i-1}$ and less than $2*T_{i-1}$, setting the second CycleTime $T_i$ to be the first CycleTime $T_{i-1}$.

In some implementations, setting the second CycleTime $T_i$ according to the interval and the first CycleTime $T_{i-1}$ includes: in response to determining that the interval is less than $T_{i-1}$, setting the second CycleTime $T_i$ to be the interval.

Determining the interval according to the second CT value, the first CT value and the first CycleTime $T_{i-1}$ can include: obtaining a CT value increasing speed according the second CT value, the first CT value and the first CycleTime $T_{i-1}$; and determining the interval according to the CT value increasing speed, the second CT value, and the target threshold.

The operations can further include: before injecting the contrast agent into the subject, performing a pilot scan on the subject to obtain a pilot image and determining the ROI according to the pilot image. The operations can also include: in response to determining that the tracking process in finished, stopping injecting the contrast agent and performing a routine CT scan to obtain a CT image of the ROI for diagnosis. For each of the CT scans, a CT value of the ROI can be a mean value of respective CT values of pixels in the ROI.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1:
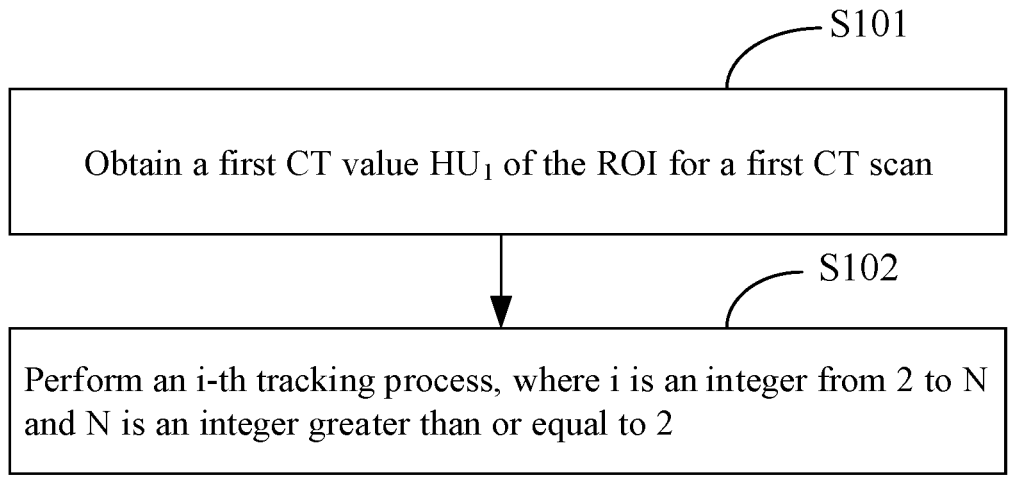
FIG. 1 is a flow diagram of a process of a CT scanning method of bolus tracking according to one or more examples of the present disclosure.

The technical solutions in examples of the present application will be clearly and completely described in the following with reference to the accompanying drawings in examples of the present application. It is apparent that the described examples are only a part of the examples of the present application, and not all of them. Based on the examples in the present application, all other examples obtained by those skilled in the art without creative efforts are within the scope of the present application.

In the bolus tracking technique, a target region of the subject is scanned repeatedly to monitor CT values, which can be represented by Hounsfield unit (HU). During the scanning process, as the number of scans increases, the radiation dose of the subject increases, and thus additional radiation damage may be brought to the subject.

To better understand the technical solutions of the present application, the bolus tracking technique is described as below. In the bolus tracking technique, multiple CT scans are performed on the target region of the subject while the contrast agent is being injected into the subject. The contrast agent is continuously injected into the subject until the concentration of the contrast agent in the target region of the subject reaches a target concentration while multiple CT scans are performed on the target region of the subject. That is, during the process of injecting the contrast agent, multiple CT scans are performed on the target region of the subject. It is determined whether the concentration of the contrast agent in the target region of the subject reaches the target concentration by performing multiple CT scans. When concentration of the contrast agent in the target region of the subject reaches the target concentration, a routine CT scan is performed to obtain a CT image for diagnosis. In this case, blood vessels in the CT image are relatively clearer.

Before the bolus tracking is performed, that is, before the contrast agent is injected into the subject, a pilot scan is performed on the subject to obtain a pilot image. A target region (may also be referred to as region of interest (ROI)) is marked on the pilot image. The ROI is a target region of bolus tracking. In an example, when the bolus tracking is performed, multiple CT scans are performed on the ROI according to a preset CycleTime and a CT value of the ROI for each CT scan is obtained. CycleTime represents a total time from a beginning of a first CT scan to a beginning of a second, sequential CT scan. The CT value of the ROI for each CT scan represents the current concentration of the contrast agent in the ROI of the subject. The CT value of the ROI is compared with a target threshold. If the CT value of the ROI is equal to the target threshold, it indicates that the concentration of the contrast agent in the ROI of the subject reaches the target concentration. When the concentration of the contrast agent in the ROI of the subject reaches the target concentration, the bolus tracking is finished. Then, a routine CT scan is performed on the ROI of the subject to obtain a CT image for diagnosis.

A CT scanning method of bolus tracking is provided in examples of the present disclosure. The CT scanning method of bolus tracking is performed after the ROI is determined based on the pilot image. In the CT scanning method of bolus tracking, the bolus tracking is performed while the contrast agent is continuously injected into the subject until the concentration of the contrast agent in the ROI of the subject reaches the target concentration.

In some implementations, the CT scanning method of bolus tracking includes:

obtaining a first CT value $HU_1$ of the ROI for a first CT scan; and performing an i-th tracking process, where i is an integer from 2 to N, N is an integer greater than or equal to 2, and the i-th tracking process includes:

obtaining an i-th CT value $HU_i$ of the ROI for an i-th CT scan, where the i-th CT scan is performed after a (i−1)-th scanning CycleTime $T_{i-1}$, an original scanning CycleTime is marked as $T_1$, the original scanning CycleTime refers to a duration between a start of a first CT scan and a start of a second CT scan, and the (i−1)-th scanning CycleTime $T_{i-1}$ refers to a duration between a start of the (i−1)-th CT scan and a start of an i-th CT scan;

if the i-th CT value $HU_i$ is greater than or equal to a target threshold, finishing the bolus tracking;

if the i-th CT value $HU_i$ is less than the target threshold, obtaining an interval $P_{i-1}$ for increasing the i-th CT value $HU_i$ to the target threshold according to the i-th CT value $HU_i$, a (i−1)-th CT value $HU_{i-1}$ and the (i−1)-th scanning CycleTime $T_{i-1}$; and if the interval $P_{i-1}$ is greater than $2*T_{i-1}$, setting an i-th scanning CycleTime $T_i$ to a value greater than the (i−1)-th scanning CycleTime $T_{i-1}$ and performing a (i+1)-th tracking process.

In the CT scanning method of bolus tracking, the object for bolus tracking is the ROI of the subject. The CT value of the ROI is a mean value of a CT value of each pixel in the ROI. In an example, it is assumed that the ROI is an arterial region in the head and neck portion of the subject, after each CT scan, scanning data of the CT scan can be obtained and the CT value of the ROI for the CT scan can be obtained from the scanning data of the CT scan.

In the present disclosure, in the entire bolus tracking process, the scanning CycleTime may be dynamically adjusted according to the interval used for increasing the i-th CT value to the target threshold. When the interval is greater than $2*T_{i-1}$, the scanning CycleTime is increased. In this way, when the CT value of the ROI reaches the target threshold, the number of CT scans can be effectively reduced, and thus radiation damage to the subject can be reduced.

To better understand the technical solution and technical effects of the present disclosure, the CT scanning method of bolus tracking provided herein will be described in conjunction with FIG. 1.

At step S101, a first CT value $HU_1$ of the ROI for a first CT scan is obtained.

Before the first CT scan is performed, the original scanning CycleTime is preset. For ease of description, the original scanning CycleTime is marked as $T_1$.

After the first CT scan is performed, scanning data of the first CT scan is obtained. The first CT value of the ROI for the first CT scan is obtained from the scanning data of the first CT scan. For ease of description, the first CT value of the ROI for the first CT scan is marked as $HU_1$.

At step S102, an i-th tracking process is performed, where i is an integer from 2 to N and N is an integer greater than or equal to 2.

The step S102 is performed repeatedly until the i-th CT value $HU_i$ is greater than or equal to the target threshold. When the i-th CT value $HU_i$ is greater than or equal to the target threshold, the bolus tracking is finished. When the i-th CT value $HU_i$ is less than the target threshold, an interval $P_{i-1}$ used for increasing the i-th CT value $HU_i$ to the target threshold is obtained according to the i-th CT value $HU_i$, a (i−1)-th CT value $HU_{i-1}$ and the (i−1)-th scanning CycleTime $T_{i-1}$. A scanning CycleTime $T_i$ is adjusted according to the interval $P_{i-1}$. In this way, the target threshold can be reached quicker and thus the number of CT scans can be reduced.

Figure 2:
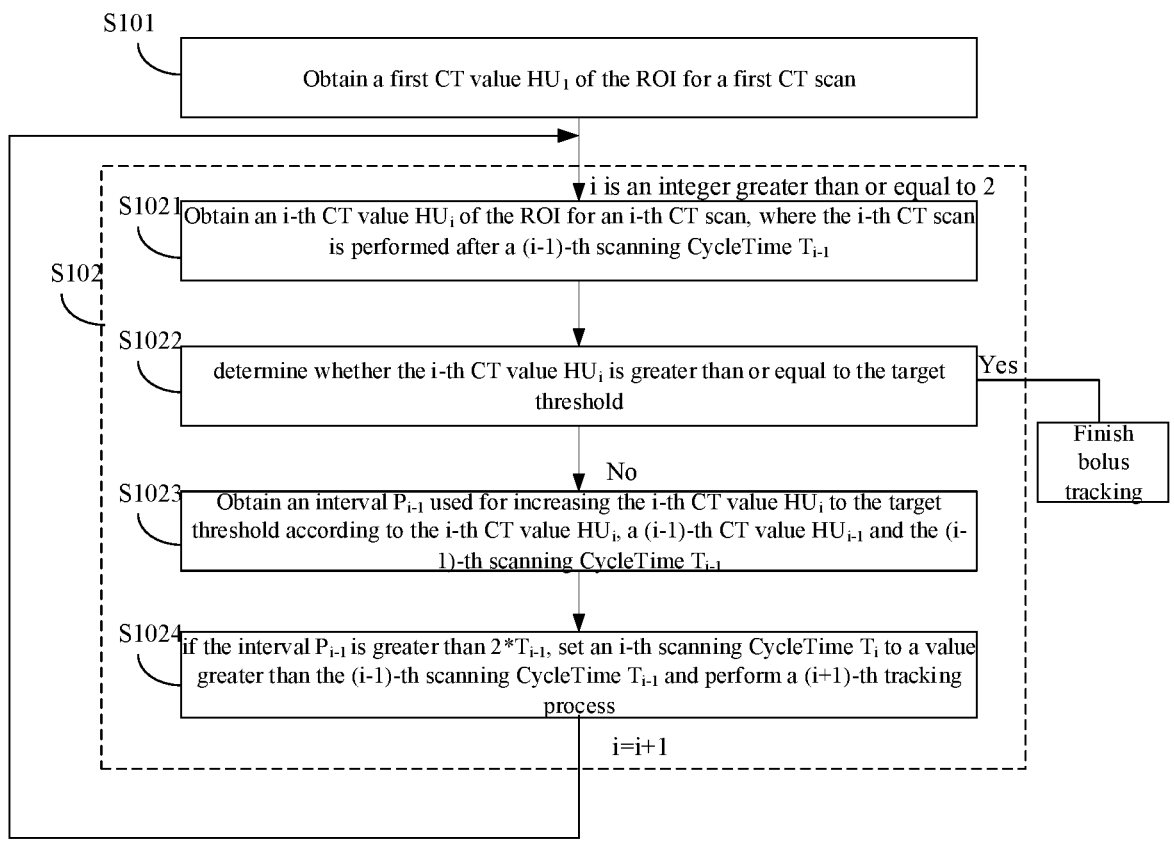
FIG. 2 is a flow diagram of an i-th tracking process according to one or more examples of the present disclosure.

FIG. 2 is a flow diagram of an i-th tracking process according to one or more examples of the present disclosure. The i-th tracking process includes steps S1021-S1024.

At step S1021, an i-th CT value $HU_i$ of the ROI for an i-th CT scan is obtained, where the i-th CT scan is performed after a (i−1)-th scanning CycleTime $T_{i-1}$.

At step S1022, it is determined whether the i-th CT value $HU_i$ is greater than or equal to the target threshold; and if the i-th CT value $HU_i$ is greater than or equal to the target threshold, the bolus tracking is finished.

The target threshold, referred to as a CT threshold, is preset. The CT threshold may be set according to empirical values. When the i-th CT value $HU_i$ is greater than or equal to the target threshold, it is determined that the concentration of the contrast agent in the ROI has reached the target concentration. The injection of the contrast agent and the bolus tracking can be ended. At this time, the CT system stops injecting the contrast agent into the subject and performs a routine CT scan on the ROI to obtain a CT image for diagnosis. That is, when the CT system stops injecting the contrast agent into the subject and performs the routine CT scan, a CT image obtained by the routine CT scan can be used to diagnose the subject.

At step S1023, if the i-th CT value $HU_i$ is less than the target threshold, an interval $P_{i-1}$ to be used for increasing the i-th CT value $HU_i$ to the target threshold is obtained according to the i-th CT value $HU_i$, a (i−1)-th CT value $HU_{i-1}$ and the (i−1)-th scanning CycleTime $T_{i-1}$.

If the i-th CT value $HU_i$ is less than the target threshold, another CT scan is required. The CT value of the ROI is positively correlated to the concentration of the contrast agent in the ROI. A CT value increasing speed can be obtained according to the i-th CT value $HU_i$, the (i−1)-th CT value $HU_{i-1}$ and the (i−1)-th scanning CycleTime $T_{i-1}$. The interval $P_{i-1}$ used for increasing the i-th CT value $HU_i$ to the target threshold can be obtained according to the CT value increasing speed.

In some cases, a CT value rising curve is obtained and then the interval $P_{i-1}$ used for increasing the i-th CT value $HU_i$ to the target threshold can be determined according to the CT value rising curve. In practical applications, as the concentration of the contrast agent in the ROI increases, the CT value of the ROI increases. The CT value of the ROI is positively correlated to the concentration of the contrast agent in the ROI. In an example, the CT value increasing speed is calculated by using a linear algorithm.

In an example, obtaining the interval $P_{i-1}$ used for increasing the i-th CT value $HU_i$ to the target threshold includes:

obtaining a (i−1)-th CT value increasing speed $HUS_{i-1}$ according to the i-th CT value $HU_i$, the (i−1)-th CT value $HU_{i-1}$ and the (i−1)-th scanning CycleTime $T_{i-1}$; and obtaining the interval $P_{i-1}$ used for increasing the i-th CT value $HU_i$ to the target threshold according to (i−1)-th CT value increasing speed $HUS_{i-1}$.

In some cases, it is assumed that the CT value of the ROI is linearly increased, the (i−1)-th CT value increasing speed $HUS_{i-1}$ is calculated by the following formula (1):

$$HUS_{i-1} = (HU_i - HU_{i-1})/T_{i-1} \qquad (1).$$

By the (i−1)-th CT value increasing speed $HUS_{i-1}$, the interval $P_{i-1}$ used for increasing the i-th CT value $HU_i$ to the target threshold is determined. The target threshold is marked as $HU_{th}$. The interval $P_{i-1}$ is calculated by the following formula (2):

$$P_{i-1} = (HU_{th} - HU_i)/HUS_{i-1} \quad (2).$$

At step S1024, if the interval $P_{i-1}$ is greater than $2*T_{i-1}$, an i-th scanning CycleTime $T_i$ is set to a value greater than the (i−1)-th scanning CycleTime $T_{i-1}$ and a (i+1)-th tracking process is performed.

At step S1024, the i-th scanning CycleTime $T_i$ is adjusted according to a relationship between the interval $P_{i-1}$ and the (i−1)-th scanning CycleTime $T_{i-1}$. In an example, when the interval $P_{i-1}$ is greater than $2*T_{i-1}$, it indicates that to reach the target threshold, more than two CT scans are needed if the same scanning CyclyTime $T_{i-1}$ is used. In this case, the i-th scanning CycleTime $T_i$ is set to a value greater than the (i−1)-th scanning CycleTime $T_{i-1}$. The (i+1)-th CT scan is performed according to the i-th scanning CycleTime $T_i$. In this way, according to the interval $P_{i-1}$ used for increasing the i-th CT value $HU_i$ to the target threshold, the i-th scanning CycleTime $T_i$ is dynamically adjusted. When the interval is greater than $2*T_{i-1}$, the i-th scanning CycleTime $T_i$ is increased. In this way, when the CT value reaches the target threshold, the number of CT scans can be effectively reduced, and thus radiation damage to the subject can be reduced.

The i-th scanning CycleTime $T_i$ is adjusted according to a particular situation. In an example, the i-th scanning CycleTime $T_i$ is a sum of the (i−1)-th scanning CycleTime $T_{i-1}$ and a preset variable. The preset variable may be a fixed value, or may also vary in accordance with a preset rule. In some cases, as the number i of CT scans increases, the preset variable can decrease gradually. In this way, as the number i of CT scans increases, the CT value more closely approaches the target threshold and an increasing amplitude of the scanning CycleTime is reduced, thereby improving the accuracy of the CT value reaching the target threshold.

In another example, the (i−1)-th scanning CycleTime $T_{i-1}$ is increased according to a preset ratio to obtain the i-th scanning CycleTime $T_i$. That is, $T_i = \rho_i*(T_{i-1})$. $\rho_i$ represents the preset ratio and is greater than 1. The preset ratio $\rho_i$ may be a fixed value, or may also vary in accordance with a preset rule. In some cases, as the number i of CT scans increases, the preset ratio $\rho_i$ decreases gradually. In this way, as the number i of CT scans increases, the CT value more closely approaches the target threshold and an increasing amplitude of the scanning CycleTime is reduced, thereby improving the accuracy of the CT value reaching the target threshold.

When the interval $P_{i-1}$ is less than or equal to $2*T_{i-1}$, the bolus tracking is continued in accordance with the (i−1)-th scanning CycleTime $T_{i-1}$. In an example, if the interval $P_{i-1}$ is less than $T_{i-1}$, the i-th scanning CycleTime $T_i$ is set to the interval $P_{i-1}$ and then the (i+1)-th CT scan is performed. In an example, when the interval $P_{i-1}$ is greater than $T_{i-1}$ and less than $2*T_{i-1}$, the i-th scanning CycleTime $T_i$ is set to the (i−1)-th scanning CycleTime $T_{i-1}$ and then the (i+1)-th CT scan is performed; and when the (i+1)-th CT scan is completed, a (i+1)-th scanning CycleTime $T_{i+1}$ is set to $(P_{i-1} - T_{i-1})$ and then a (i+2)-th CT scan is performed. In this way, when the (i+2)-th CT scan is completed, the (i+2)-th CT value $HU_{i+2}$ of the ROI for the (i+2)-th CT scan is equal to the target threshold.

Figure 3:
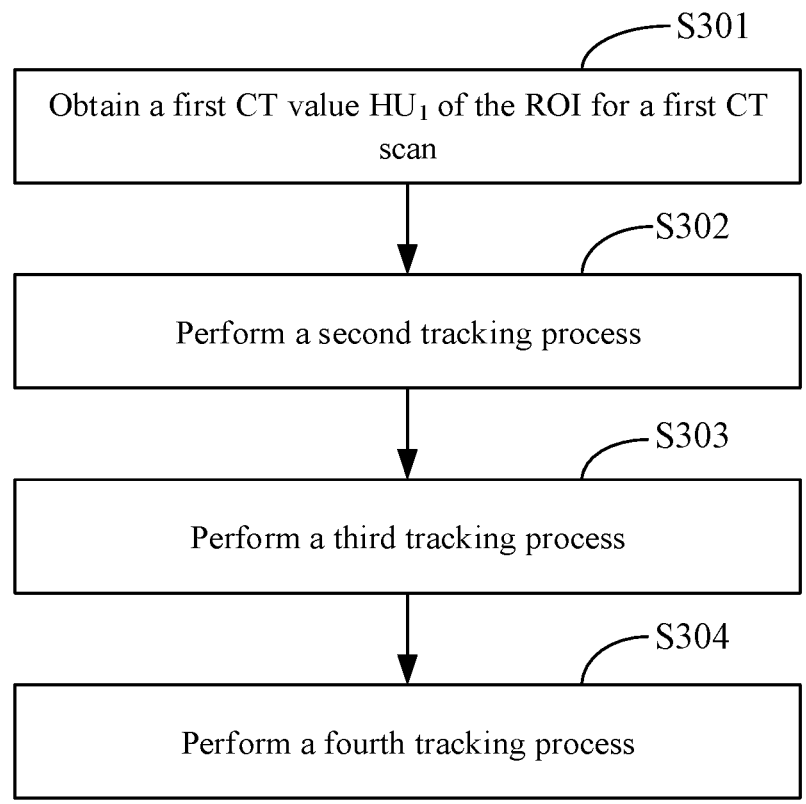
FIG. 3 is a flow diagram of a process of a CT scanning method of bolus tracking according to one or more examples of the present disclosure.

FIG. 3 is a flow diagram of a process of a CT scanning method of bolus tracking according to one or more examples of the present disclosure. For ease of understanding, four number of CT scans are taken as an example. The process as shown in FIG. 3 includes steps S301-S304.

At step S301, a first CT value $HU_1$ of the ROI for a first CT scan is obtained.

At step S302, a second tracking process is performed.

The second tracking process includes: obtaining a second CT value $HU_2$ of the ROI for a second CT scan; determining the second CT value $HU_2$ is less than a target threshold $HU_{th}$; obtaining a first CT value increasing speed $HUS_1$ according to the second CT value $HU_2$, the first CT value $HU_1$ and a first scanning CycleTime $T_1$, for example, $HUS_1 = (HU_2 - HU_1)/T_1$; obtaining an interval $P_1$ used for increasing the second CT value $HU_2$ to the target threshold $HU_{th}$ according to the first CT value increasing speed $HUS_1$, for example, $P_1 = (HU_{th} - HU_2)/HUS_1$; determining that the interval $P_1$ is greater than $2*T_1$; and setting a second scanning CycleTime $T_2$ to a value greater than first scanning CycleTime $T_1$, for example, $T_2 = T_1 + T_{1buf}$, or $T_2 = \rho_2*T_1$. The first scanning CycleTime $T_1$ refers to a duration between a start of the first CT scan and a start of the second CT scan. The second scanning CycleTime $T_2$ refers to a duration between the start of the second CT scan and a start of a third CT scan.

At step S303, a third tracking process is performed.

The third tracking process includes: obtaining a third CT value $HU_3$ of the ROI for a third CT scan; determining the third CT value $HU_3$ is less than the target threshold $HU_{th}$; obtaining a second CT value increasing speed $HUS_2$ according to the third CT value $HU_3$, the second CT value $HU_2$ and the second scanning CycleTime $T_2$, for example, $HUS_2 = (HU_3 - HU_2)/T_2$; obtaining an interval $P_2$ used for increasing the third CT value $HU_3$ to the target threshold $HU_{th}$ according to the second CT value increasing speed $HUS_2$, for example, $P_2 = (HU_{th} - HU_3)/HUS_2$; determining that the interval $P_2$ is less than the second scanning CycleTime $T_2$; and setting a third scanning CycleTime $T_3$ to be the interval $P_2$. The third scanning CycleTime $T_3$ refers to a duration between the start of the third CT scan and a start of a fourth CT scan.

At step S304, a fourth tracking process is performed.

The fourth tracking process includes: obtaining a fourth CT value $HU_4$ of the ROI for a fourth CT scan; determining that the fourth CT value $HU_4$ is equal to the target threshold; and finishing the bolus tracking.

It is understood that the above examples are illustrative only and that the present disclosure is not limited thereto.

The CT scanning method of bolus tracking is provided. In the CT scanning method of bolus tracking, multiple CT scans are performed on a ROI of a subject while a contrast agent is being injected into the subject, so as to perform a tracking process of the contrast agent. In an example, the method includes:

obtaining a first CT value of the ROI of the subject for a (i−1)-th CT scan, where i is an integer greater than or equal to 2, and a duration between a start of a first CT scan and a start of a second CT scan is preset;

obtaining a second CT value of the ROI of the subject for an i-th CT scan, where a duration between a start of the i-th CT scan and a start of the (i−1)-th CT scan is marked as a first CycleTime $T_{i-1}$;

if the second CT value is greater than or equal to a target threshold, finishing the tracking process;

if the second CT value is less than the target threshold, determining an interval according to the second CT value, the first CT value and the first CycleTime $T_{i-1}$, where the interval is required for increasing the second CT value to the target threshold;

setting a second CycleTime $T_i$ according to the interval and the first CycleTime $T_{i-1}$, where the second CycleTime $T_i$ indicates a duration between the start of the i-th CT scan and a start of a (i+1)-th CT scan; and performing the (i+1)-th CT scan according to the second CycleTime $T_i$ so as to update the first CT value and the second CT value of the ROI of the subject, until the tracking process is finished.

In this way, in the entire tracking process, the scanning CycleTime may be dynamically adjusted according to the interval used for increasing the i-th CT value to the target threshold. When the interval is greater than $2*T_{i-1}$, the scanning CycleTime is increased. In this way, when the CT value reaches the target threshold, the number of CT scans can be effectively reduced, and thus radiation damage to the subject can be reduced.

Figure 4:
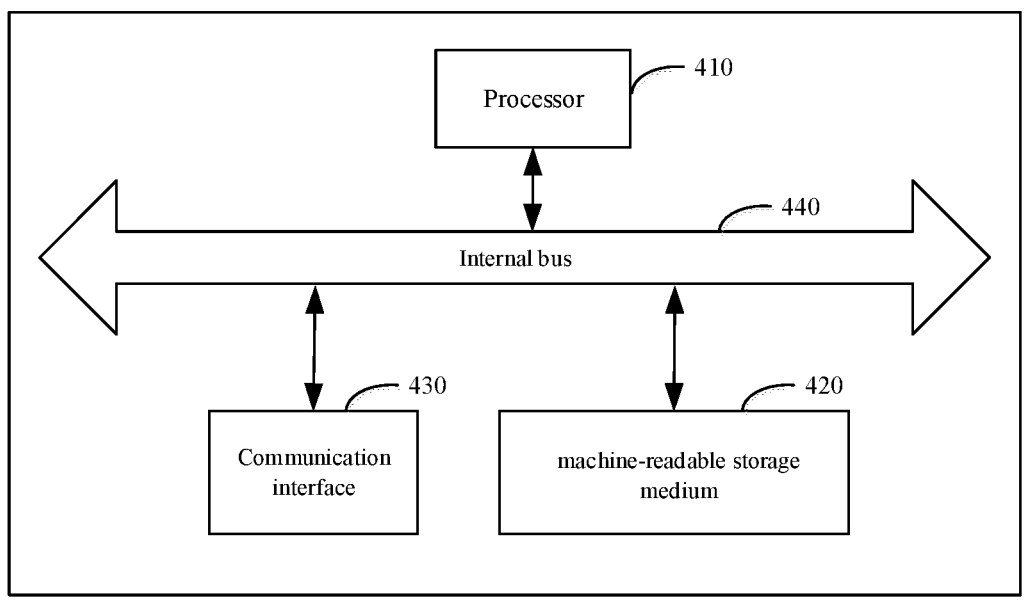
FIG. 4 is a schematic diagram of an example hardware structure of a device for bolus tracking.

Corresponding to the above-mentioned CT scanning method of bolus tracking, a device for bolus tracking is further provided. FIG. 4 is a hardware structural diagram of a device for bolus tracking according to an example. Referring to FIG. 4, the device includes a processor 410, a machine readable storage medium 420, a communication interface 430 and a bus 440. The processor 410, the communication interface 430, and the machine readable storage medium 420 communicate with each other via the bus 440. The device can include other hardware according to actual needs, and the present disclosure does not limit this.

In some cases, the machine readable storage medium includes RAM (Random Access Memory), non-transitory machine readable storage medium, flash memory, storage drive (such as a hard drive), solid state drive, any type of storage disk (such as CD, DVD, etc.), or similar storage medium, or a combination thereof.

In an example, by invoking machine executable instructions stored in the machine readable storage medium 420, the processor 410 is caused to perform the CT scanning method of bolus tracking. Details may refer to the above CT scanning method of bolus tracking, which are omitted for brevity.

In an example, a non-transitory machine readable storage medium is also provided. The non-transitory machine readable storage medium stores machine executable instructions which are executed by one or more processors. The machine executable instructions are executed by the processor to perform the CT scanning method of bolus tracking. Details may refer to the above CT scanning method of bolus tracking, which are omitted for brevity.

For the device example, since it basically corresponds to the method example, it can be referred to the description of the method example. The device example described above is merely illustrative, wherein the units described as separate components may or may not be physically separated, and the components displayed as units may or may not be physical units, they may be located a place, or distributed to multiple network units. Some or all of the modules may be selected according to actual needs to implement the purpose of the technical solution of the present disclosure. Those of ordinary skill in the art can understand and implement without any creative effort.

It should be appreciated that although different information may be described using the terms such as first, second, third, etc. in the present disclosure, such information should not be limited to these terms. Such terms are used only to distinguish the same type of information from each other.

For example, without departing from the scope of the present disclosure, the first information may also be referred to as the second information and similarly, the second information may also be referred to as the first information. Depending on the context, the word "if" as used herein may be interpreted as "when" or "as" or "in response to determining".

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other examples are within the scope of the following claims.

What is claimed is:

1. A CT scanning method of bolus tracking, in which multiple CT scans are performed on a region of interest (ROI) of a subject while a contrast agent is injected into the subject, to perform a tracking process of the contrast agent, the method comprising:

obtaining a first CT value of the ROI of the subject for a (i−1)-th CT scan, wherein i is an integer greater than or equal to 2;

obtaining a second CT value of the ROI of the subject for an i-th CT scan, wherein a first CycleTime $Ti_{i-1}$ represents a duration between a start of the i-th CT scan and a start of the (i−1)-th CT scan, and $T_1$ is preset;

determining whether the second CT value is no less than a target threshold; and in response to determining that the second CT value is less than the target threshold, determining an interval required to increase the second CT value to the target threshold according to the second CT value, the first CT value and the first CycleTime $T_{i-1}$;

setting a second CycleTime $T_i$ according to the interval and the first CycleTime $T_{i-1}$, wherein the second CycleTime $T_i$ represents a duration between the start of the i-th CT scan and a start of a (i+1)-th CT scan; and performing the (i+1)-th CT scan according to the second CycleTime $T_i$, wherein setting the second CycleTime $T_i$ according to the interval and the first CycleTime $T_{i-1}$ comprises:

in response to determining that the interval is greater than $2*T_{i-1}$, setting the second CycleTime $T_i$ to be a value greater than the first CycleTime $T_{i-1}$.

2. The method of claim 1, wherein the value greater than the first CycleTime $T_{i-1}$ is a sum of the first CycleTime $T_{i-1}$ and a preset variable, and wherein the preset variable decreases gradually as a number of CT scans performed on the ROI of the subject increases.

3. The method of claim 1, wherein the first CycleTime $T_{i-1}$ is increased according to a preset ratio to obtain the value greater than the first CycleTime $T_{i-1}$, and wherein the preset ratio decreases gradually as a number of CT scans performed on the ROI of the subject increases.

4. The method of claim 1, wherein setting the second CycleTime $T_i$ according to the interval and the first CycleTime $T_{i-1}$ comprises:
in response to determining that the interval is greater than $T_{i-1}$ and less than $2*T_{i-1}$, setting the second CycleTime $T_i$ to be the first CycleTime $T_{i-1}$.

5. The method of claim 1, wherein setting the second CycleTime $T_i$ according to the interval and the first CycleTime $T_{i-1}$ comprises:
in response to determining that the interval is less than $T_{i-1}$, setting the second CycleTime $T_i$ to be the interval.

6. The method of claim 1, wherein determining the interval according to the second CT value, the first CT value and the first CycleTime $T_{i-1}$ comprises:
obtaining a CT value increasing speed according the second CT value, the first CT value and the first CycleTime $T_{i-1}$; and
determining the interval according to the CT value increasing speed, the second CT value, and the target threshold.

7. The method of claim 1, further comprising:
before injecting the contrast agent into the subject, performing a pilot scan on the subject to obtain a pilot image and determining the ROI according to the pilot image.

8. The method of claim 1, further comprising:
determining that the tracking process is finished when a CT value of the ROI of the subject obtained for a CT scan is no less than the target threshold, and in response,
stopping injecting the contrast agent and performing a routine CT scan to obtain a CT image of the ROI for diagnosis.

9. The method of claim 1, wherein, for each of the CT scans, a CT value of the ROI is a mean value of respective CT values of pixels in the ROI.

10. A device for bolus tracking, comprising:
at least one processor; and
at least one non-transitory machine-readable storage medium coupled to the at least one processor having machine-executable instructions stored thereon that, when executed by the at least one processor, cause the at least one processor to perform operations for bolus tracking, in which multiple CT scans are performed on a region of interest (ROI) of a subject while a contrast agent is injected into the subject, to perform a tracking process of the contrast agent, the operations comprising:
obtaining a first CT value of a ROI of a subject for a (i−1)-th CT scan, wherein i is an integer greater than or equal to 2;
obtaining a second CT value of the ROI of the subject for an i-th CT scan, wherein a first CycleTime $T_{i-1}$ represents a duration between a start of the i-th CT scan and a start of the (i−1)-th CT scan, and T1 is preset;
determining whether the second CT value is no less than a target threshold;
in response to determining that the second CT value is greater than or equal to the target threshold, ending the tracking process; and
in response to determining that the second CT value is less than the target threshold,
determining an interval required to increase the second CT value to the target threshold according to the second CT value, the first CT value and the first CycleTime $T_{i-1}$,
setting a second CycleTime $T_i$ according to the interval and the first CycleTime $T_{i-1}$, wherein the second CycleTime $T_i$ represents a duration between the start of the i-th CT scan and a start of a (i+1)-th CT scan; and
performing the (i+1)-th CT scan according to the second CycleTime $T_i$,
wherein setting the second CycleTime $T_i$ according to the interval and the first CycleTime $T_{i-1}$ comprises:
in response to determining that the interval is greater than $2*T_{i-1}$, setting the second CycleTime $T_i$ to be a value greater than the first CycleTime $T_{i-1}$.

11. The device of claim 10, wherein the value greater than the first CycleTime $T_{i-1}$ is a sum of the first CycleTime and a preset variable, and
wherein the preset variable decreases gradually as a number of CT scans performed on the ROI of the subject increases.

12. The device of claim 10, wherein the first CycleTime $T_{i-1}$ is increased according to a preset ratio to obtain the value greater than the first CycleTime $T_{i-1}$, and
wherein the preset ratio decreases gradually as a number of CT scans performed on the ROI of the subject increases.

13. The device of claim 10, wherein setting the second CycleTime $T_i$ according to the interval and the first CycleTime $T_{i-1}$ comprises:
in response to determining that the interval is greater than $T_{i-1}$ and less than $2*T_{i-1}$, setting the second CycleTime $T_i$ to be the first CycleTime $T_{i-1}$.

14. The device of claim 10, wherein setting the second CycleTime $T_i$ according to the interval and the first CycleTime $T_{i-1}$ comprises:
in response to determining that the interval is less than $T_{i-1}$, setting the second CycleTime $T_i$ to be the interval.

15. The device of claim 10, wherein determining the interval according to the second CT value, the first CT value and the first CycleTime $T_{i-1}$ comprises:
obtaining a CT value increasing speed according the second CT value, the first CT value and the first CycleTime $T_{i-1}$; and
determining the interval according to the CT value increasing speed, the second CT value, and the target threshold.

16. The device of claim 10, wherein the operations further comprise:
before injecting the contrast agent into the subject, performing a pilot scan on the subject to obtain a pilot image and determining the ROI according to the pilot image.

17. The device of claim 10, wherein the operations further comprise:
in response to determining that the tracking process is finished, stopping injecting the contrast agent and performing a routine CT scan to obtain a CT image of the ROI for diagnosis.

18. The device of claim 10, wherein, for each of the CT scans, a CT value of the ROI is a mean value of respective CT values of pixels in the ROI.

* * * * *